US010955654B2

(12) United States Patent
Chenegros et al.

(10) Patent No.: US 10,955,654 B2
(45) Date of Patent: Mar. 23, 2021

(54) IMAGING DEVICE AND METHOD

(71) Applicants: UNIVERSITE PIERRE ET MARIE CURIE (PARIS 6), Paris (FR); CENTRE NATIONAL DE LA RECHERCHE SCIENTIFIQUE—CNRS, Paris (FR); INSERM (INSTITUT NATIONAL DE LA SANTE ET DE LA RECHERCHE MEDICALE), Paris (FR); UNIVERSITE PARIS—SUD, Orsay (FR); ASSISTANCE PUBLIQUE-HOPITAUX DE PARIS—APHP, Paris (FR)

(72) Inventors: Guillaume Chenegros, Trappes (FR); Ryad Benosman, Paris (FR); Nicolas Libert, Paris (FR); Jacques Durenteau, Paris (FR); Anatole Harrois, Fontenay sous Bois (FR); Serge Picaud, Avon (FR); Jose-Alain Sahel, Paris (FR)

(73) Assignees: SORBONNE UNIVERSITÉ, Paris (FR); CENTRE NATIONAL DE LA RECHERCHE SCIENTIFIQUE—CNRS, Paris (FR); INSERM (INSTITUT NATIONAL DE LA SANTE ET DE LA RECHERCHE MEDICALE), Paris (FR); UNIVERSITE PARIS-SUD, Orsay (FR); ASSISTANCE PUBLIQUE-HOPITAUX DE PARIS—APHP, Paris (FR)

(*) Notice: Subject to any disclaimer, the term of this patent is extended or adjusted under 35 U.S.C. 154(b) by 588 days.

(21) Appl. No.: 15/539,320

(22) PCT Filed: Dec. 16, 2015

(86) PCT No.: PCT/FR2015/053537
§ 371 (c)(1),
(2) Date: Jun. 23, 2017

(87) PCT Pub. No.: WO2016/102819
PCT Pub. Date: Jun. 30, 2016

(65) Prior Publication Data
US 2018/0024343 A1 Jan. 25, 2018

(30) Foreign Application Priority Data
Dec. 24, 2014 (FR) ........................ 14 63335

(51) Int. Cl.
*A61B 5/00* (2006.01)
*G02B 21/36* (2006.01)
(Continued)

(52) U.S. Cl.
CPC .......... *G02B 21/361* (2013.01); *A61B 5/0077* (2013.01); *A61B 5/0261* (2013.01);
(Continued)

(58) Field of Classification Search
CPC ........................ G02B 21/361; A61B 5/0077
See application file for complete search history.

(56) References Cited

U.S. PATENT DOCUMENTS 8,644,911 B1    2/2014  Panasyuk et al.
2004/0008867 A1* 1/2004  Fein .................. G01N 21/6458
                                             382/100
(Continued)

FOREIGN PATENT DOCUMENTS

CN    101900875 A    12/2010
CN    103356174 A    10/2013
(Continued)

OTHER PUBLICATIONS

Patrick Lichtsteiner, et al., A 128 X 128 120 dB 15 μs Latency Asynchronous Temporal Contrast Vision Sensor, IEEE Journal of Solid-State Circuits, Feb. 2008, pp. 566-576, vol. 43, No. 2.
(Continued)

*Primary Examiner* — Joseph M Santos Rodriguez
(74) *Attorney, Agent, or Firm* — Nixon & Vanderhye

(57) ABSTRACT

Disclosed is an imaging device including a light source arranged so as to generate an optical signal, an optical support coupled to the light source and arranged so as to project a luminous excitation signal with a substantially
(Continued)

constant light intensity, from the light source to a body to be observed during the use of the device, and an asynchronous camera coupled to the optical support and designed so as to generate a signal including, for each pixel of a first pixel matrix, a signal sequence representing asynchronous events corresponding to variations of the light backscattered by the body to be observed for the pixel.

10 Claims, 7 Drawing Sheets

(51) Int. Cl.
    *A61B 5/026*    (2006.01)
    *G01N 21/47*    (2006.01)
    *A61B 5/1455*    (2006.01)
    *G01N 21/53*    (2006.01)
    *G02B 21/06*    (2006.01)

(52) U.S. Cl.
    CPC ........ *A61B 5/14556* (2013.01); *A61B 5/7285* (2013.01); *G01N 21/474* (2013.01); *G01N 21/53* (2013.01); *G02B 21/06* (2013.01); *G01N 2021/4709* (2013.01); *G01N 2021/4759* (2013.01); *G01N 2201/062* (2013.01); *G01N 2201/06113* (2013.01)

(56) References Cited

U.S. PATENT DOCUMENTS

2006/0184037 A1* 8/2006 Ince ...................... A61B 1/042
    600/476
2008/0135731 A1 6/2008 Lichtsteiner et al.

FOREIGN PATENT DOCUMENTS

| | | |
|---|---|---|
| CN | 103445764 A | 12/2013 |
| EP | 2 515 153 A1 | 10/2012 |
| WO | 2005032361 A2 | 4/2005 |

OTHER PUBLICATIONS

Christopher Posch, et al., A QVGA 143 dB Dynamic Range Frame-Free PWM Image Sensor With Lossless Pixel-Level Video Compression and Time-Domain CDS, IEEE Journal of Solid-State Circuits, Jan. 2011, pp. 259-275, vol. 46, No. 1.
Christopher Posch, et al., An Asynchronous Time-based Image Sensor, IEEE International Symposium on Circuits and Systems, Jun. 2008, pp. 2130-2133.
Mar. 14, 2016, International Search Report issued for International Application No. PCT/FR2015/053537.
De Backer et al., Microvascular Blood Flow Is Altered in Patients with Sepsis, American Journal of Respiratory and Critical Care Medicine, 2002, vol. 166, pp. 98-104.
Pranskunas et al., Microcirculatory blood flow as a tool to select ICU patients eligible for fluid therapy, Intensive Care Med, 2013, vol. 39, pp. 612-619.
Nagaoka et al., Relationship Between Retinal Blood Flow and Renal Function in Patients With Type 2 Diabetes and chronic Kidney Disease, Diabetes Care, 2013, vol. 36, pp. 957-961.
Pemp et al., Ocular blood flow in diabetes and age-related macular degeneration, Can J Ophthalmol, 2008, vol. 43, pp. 295-301.
Wong et al., Retinal Arteriolar Narrowing and Risk of Coronary Heart Disease in Men and Women, The Atherosclerosis Risk in Communities Study, JAMA, 2002, vol. 287, pp. 153-1159.
Cheung et al., Retinal Arteriolar Narrowing and Left Ventricular Remodeling, The Multi-Ethnic Study of Atherosclerosis, Journal of The American College of Cardiology, 2007, vol. 50, pp. 48-55.
Wong et al., Retinal Microvascular Abnormalities and Cognitive Impairment in Middle-Aged Persons, The Atherosclerosis Risk in Communities Study, Stroke, 2002, vol. 33, pp. 1487-1492.
Wang et al., Transient Ischemic Attack and Acute Ischemic Stroke, Associations With Retinal Microvascular Signs, Stroke, 2011, vol. 42, pp. 404-408.
Maude et al., The spectrum of retinopathy in adults with Plasmodium falciparum malaria, Transactions of the Royal Society of Tropical Medicine and Hygiene, 2009, vol. 103, pp. 665-671.
Rosenfeld et al., Early management of severe traumatic brain injury, Lancet, 2012, vol. 380, pp. 1088-1098.
Roger et al., American Heart Association Statistics Committee and Stroke Statistics Subcommittee, Heart Disease and Stroke Statistics—2012 Update, A Report From the American Heart Association, Circulation, 2012, vol. 125, pp. a2-e220.
Yau et al., Meta-Analysis for Eye Disease (META-EYE) Study Group, Global Prevalence and Major Risk Factors of Diabetic Retinopathy, Diabetes Care, 2012, vol. 35, pp. 556-564.
Klein et al., The Prevalence of Age-Related Macular Degeneration and Associated Risk Factors, Arch Ophthalmol, 2010, vol. 128, pp. 750-758.
Busskamp et al., Genetic Reactivation of Cone Photoreceptors Restores Visual Responses in Retinitis Pigmentosa, Science, vol. 329, pp. 413-417.
Busskamp et al., Optogenetic therapy for retinitis pigmentosa, Gene Therapy, 2012, vol. 19, pp. 169-175.
Fradot et al., Gene Therapy in Ophthalmology: Validation on Cultured Retinal Cells and Explants from Postmortem Human Eyes, Human Gene Therapy, 2011, vol. 22, pp. 587-593.
Harrois et al., Synergistic Deleterious Effect of Hypoxemia and Hypovolemia on Microcirculation in Intestinal Villi, Crit Care Med, 2013, vol. 41, pp. e376-e384.
Soubeyrand et al., Rat model of spinal cord injury preserving dura mater integrity and allowing measurements of cerebrospinal fluid pressure and spinal cord blood flow, Eur Spine J, 2013, vol. 22, pp. 1810-1819.
Harrois et al., Targeting the microcirculation in resuscitation of acutely unwell patients, Current Opinion in Critical Care, 2011, vol. 17, pp. 303-307.
Sakr et al., Persistent microcirculatory alterations are associated with organ failure and death in patients with septic shock, Crit Care Med, 2004, vol. 32, pp. 1825-1831.
Trzeciak et al., Early increases in microcirculatory perfusion during protocol-directed resuscitation are associated with reduced multiorgan failure at 24 h in patients with sepsis, Microcirculatory alterations in resuscitation and shock (mars) investigators, Intensive Care Med, 2008, vol. 34, pp. 2210-2217.
Bezemer et al., Clinical review: Clinical imaging of the sublingual microcirculation in the critically ill—where do we stand?, Critical Care, 2012, vol. 16, pp. 1-9.
Bateman et al., Microvascular resuscitation as a therapeutic goal in severe sepsis, Critical Care, 2005, vol. 9, pp. S27-S32.
Stern, In vivo evaluation of microcirculation by coherent light scattering, Nature, 1975, vol. 254, pp. 56-58.
Bonner et al., Model for laser Doppler measurements of blood flow in tissue, Applied Optics, 1981, vol. 20, pp. 2097-2107.
Jöbsis, Noninvasive, Infrared Monitoring of Cerebral and Myocardial Oxygen Sufficiency and Circulatory Parameters, Science, 1977, vol. 198, pp. 1264-1267.
Christ et al., Different Optical Methods for Clinical Monitoring of the Microcirculation, European Surgical Research, 2002, vol. 34, pp. 145-151.
Backer et al., Monitoring the microcirculation in the critically ill patient: current methods and future approaches, 2010, vol. 36, pp. 1813-1825.
Goedhart et al., Sidestream Dark Field (SDF) imaging: a novel stroboscopic LED ring-based imaging modality for clinical assessment of the microcirculation, 2007, vol. 15, pp. 15101-15114.
Plyer et al., Massively Parallel Lucas Kanade optical ow for real-time video processing applications, J Real-Time Image Proc, Springer, 2014, 18 pages.
Romagnoli et al., Microcirculation in clinical practice, OA Anaesthetics, 2013, pp. 1-6.

(56) References Cited

OTHER PUBLICATIONS

ČernÝ et al., Orthogonal Polarization Spectral Imaging, Physiological Research, 2007, vol. 56, pp. 141-147.
Lichtsteiner et al., a 128x128 120 dB 15 μs. Latency Asynchronous Temporal Contrast Vision Sensor, IEEE, 2008, pp. 1-24.
Lagorce et al., Asynchronous Event-Based Multi-kernel Algorithm for High Speed Visual Features Tracking, 2014, pp. 1-1.
Handa et al., Real-Time Camera Tracking: When is High Frame-Rate Best?, 2012, pp. 1-14.

* cited by examiner

IMAGING DEVICE AND METHOD

BACKGROUND OF THE INVENTION

Field of the Invention

This invention relates to imaging devices, and more particularly to imaging devices for studying the microcirculation of the blood.

Description of the Related Art

Different video-microscopic imaging techniques have been developed for monitoring microcirculation and more generally for studying circulation in blood vessels having a diameter of about one µm. These techniques allow us to view, for example, the movement of blood cells, and in particular that of red blood cells in blood vessels, in particular blood capillaries.

The OPS or Orthogonal Polarization Spectral technique uses an incident light beam, linearly polarised in a plane, which is projected on the subject through a beam splitter. The analysis is performed on the reflected light, the polarisation of which is modified according to the degree of depth of penetration of the incident light in the tissues before being reflected. A large portion of the reflected light originates from the reflection by the upper layers of the tissues observed, and keeps its initial polarisation, whereas the incident light that penetrates more deeply into the tissues observed, therefore undergoes scattering and loses its initial polarisation. The analysis device comprises a camera having a lens, in front of which is positioned an orthogonal polariser that blocks the portion of reflected light that has kept its polarisation, in order to generate an image from the reflected light not filtered by the polariser.

The SDF or Sidestream Dark Field technique uses a dark-field illumination provided through a circular prismatic lens arranged surrounding the lens of a camera, in order to generate a halo of light around and beyond the focal point of the lens. The camera is typically located above a central area of the halo of light in order to capture the backscattered light. This type of illumination, which gives a deeper depth of observation and a three-dimensional image of the tissues observed, seems to be well suited to applications analysing the microcirculation of blood.

One example of an imaging device for capturing images of the functional microcirculation system using the principle of dark-field microscopy is disclosed in the international patent application published under number WO 2005/032361 A2.

Existing imaging devices capturing images of the functional microcirculation system however, do not allow for the observation of rapid phenomena such as the circulation of red blood cells. Moreover, limits exist when observing and analysing microcirculation in real-time.

There is also a need for imaging devices that do not have the aforementioned drawbacks of conventional devices. In particular, a first need involves providing imaging devices that allow for the observation of rapid phenomena linked to the microcirculation of blood, such as the movement of red blood cells. There is a further need to provide imaging devices that allow for the real-time processing of generated information in order to analyse the microcirculation of blood.

BRIEF SUMMARY OF THE INVENTION

According to a first aspect, the invention proposes an imaging device comprising at least one light source arranged so as to generate an optical signal, an optical support coupled to the light source and arranged so as to project a luminous excitation signal with a substantially constant light intensity, from the light source to a body to be observed during the use of the device, and a first asynchronous camera coupled to the optical support and designed so as to generate a signal comprising, for each pixel of a first pixel array, a signal sequence representing asynchronous events corresponding to variations of the light backscattered by the body to be observed for the pixel.

The use of an asynchronous camera for capturing images of rapid phenomena, in particular biological phenomena, has many advantages. Such advantages are in particular the result of video acquisition that is not controlled by a clock, but by the events occurring for each pixel of the sensor in the scene opposite which the sensor is placed. Conversely, conventional cameras are, through control and synchronisation signals generated by the sensor from a clock frequency, signals that are in no way linked to the source of the visual information. This operating mode is radically different from asynchronous cameras and allows much higher temporal resolution values to be obtained than conventional cameras, which allows for the implementation of imaging systems having high spatial and temporal resolutions with sufficient sensitivity to pave the way for new possibilities in observing and analysing rapid biological phenomena such as microcirculation.

Moreover, methods for acquiring or synthesising an image sequence by frames have the drawback of producing data with a high redundancy, due to the fact that each frame represents a large number of pixels of an image if said image is not whole, and because all of these pixels, for which there are no information changes from one image to another, generate redundancies in the data representing the image sequence. This redundancy can only be partially deleted by the compressed encoding of a standard video signal. Conversely, the asynchronous signals generated by the asynchronous cameras are designed to obtain a very compact representation of data regarding an image sequence, because said data, representing events for one pixel (and not for all pixels of an array or for a large number of the latter), is not redundant from one image to another.

In one embodiment, the imaging device can comprise a second asynchronous camera coupled to the optical support and designed so as to generate a signal comprising, for each pixel of a second pixel array, a signal sequence representing asynchronous events corresponding to variations in the light backscattered by the body to be observed for the pixel, and wherein a first optical filter is arranged so as to filter the backscattered light captured by the first asynchronous camera.

The use of a second asynchronous camera allows certain types of analyses to be performed, such as spectral analysis, which uses the properties of the acquired backscattered light for the same observation for different wavelengths.

Alternatively, the first optical filter can be used to filter the backscattered light captured by the first asynchronous camera, and a second optical filter can also be arranged so as to filter the backscattered light captured by the second asynchronous camera. This allows the light to be selected according to its wavelength so that each asynchronous camera substantially simultaneously receives the information from the body studied.

In one embodiment, the imaging device can comprise a third asynchronous camera coupled to the optical support and designed so as to generate a signal comprising, for each pixel of a third pixel array, a signal sequence representing asynchronous events corresponding to variations in the light backscattered by the body to be observed for the pixel, and wherein a third optical filter is arranged so as to filter the backscattered light captured by the third asynchronous camera.

In one embodiment, the light source can be a light-emitting diode, for example stimulated by a DC voltage, or a laser source.

In one embodiment, the device can comprise a plurality of light sources arranged on the optical support so as to generate luminous excitation signals with substantially constant respective light intensities. The light intensity can be different from one light source to another, and the embodiment wherein the light sources have the same substantially constant light intensity is a non-limiting example embodiment of the device proposed.

Moreover, the light sources can be arranged on the optical support such that they form a luminous ring.

In one embodiment, the one or more asynchronous cameras can be arranged on the support located above an area that is not illuminated by the one or more light sources.

According to another aspect, a microcirculation imaging system comprising a device according to the different embodiments described herein is proposed.

According to another aspect, an imaging method is proposed, comprising the steps of: generating an optical signal with a substantially constant light intensity;

projecting a luminous excitation signal from the optical signal to a body to be observed; and generating a signal comprising, for each pixel of a first pixel array, a signal sequence representing asynchronous events corresponding to variations of the light backscattered by the body to be observed for the pixel.

BRIEF DESCRIPTION OF THE DRAWINGS

Other specific features and advantages of this invention will become apparent from the description below of non-limiting example embodiments, provided with reference to the appended figures, wherein:

FIG. 3b shows an example of a signal emitted by the asynchronous sensor in response to the intensity profile in FIG. 3a;

FIG. 7a is a block diagram of an imaging device according to one embodiment of the device proposed;

FIG. 7b is a block diagram of portions of the imaging device in FIG. 7a;

DETAILED DESCRIPTION OF THE PREFERRED EMBODIMENTS

In the detailed description below of embodiments of the invention, numerous specific details are presented for a more comprehensive understanding. Nonetheless, one of ordinary skill in the art can understand that embodiments can be implemented without these specific details. In other cases, well-known characteristics are not described in detail to prevent the description from being needlessly complicated.

The term "body" is understood herein as human or animal tissue, for example when using the device proposed for capturing images of the microcirculation system, or of any object that is to be observed, using the imaging device proposed or the imaging method proposed.

The invention will be described hereinbelow within the non-limiting scope of an asynchronous information item representing, for a pixel of a pixel array, events corresponding to variations in light for the pixel. The devices and systems proposed are not however limited to this specific embodiment, whereby the events concerning the pixel can, depending on the embodiment, correspond to variations in light for the pixel, upon the detection of a form of interest or upon the detection of a primitive, and more generally to any type of asynchronous information for the pixel.

Figure 1:
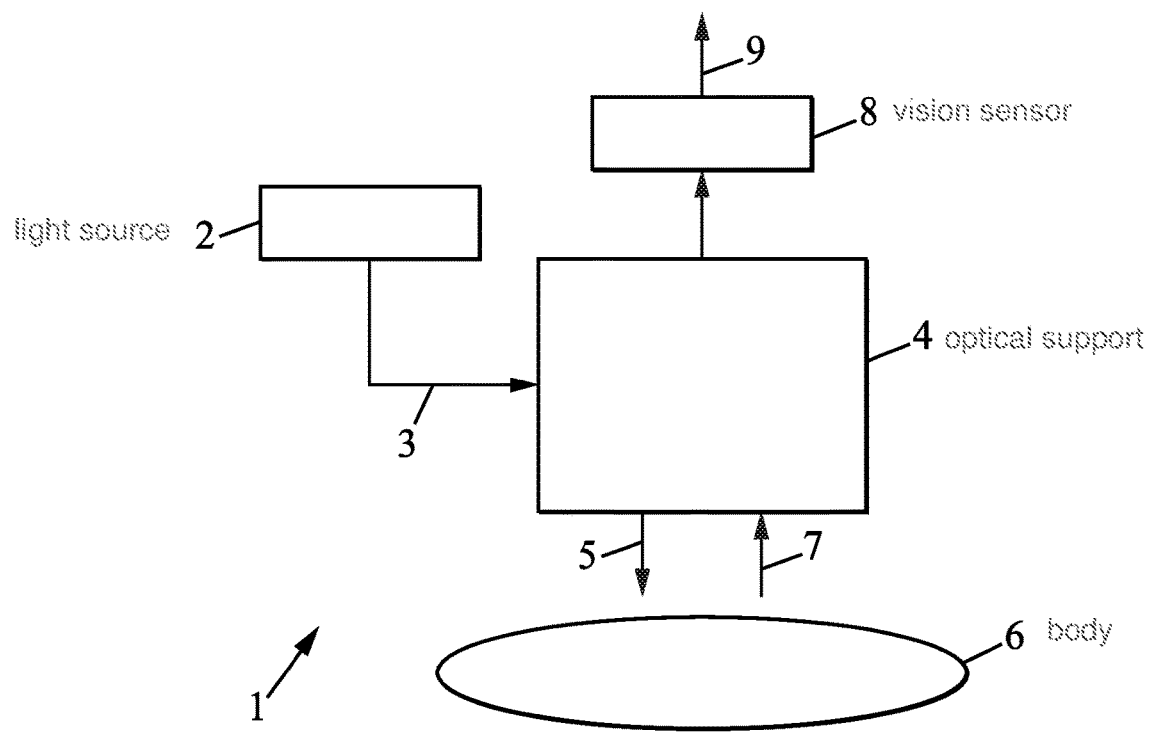
FIG. 1 is a block diagram of an imaging device according to one embodiment of the device proposed.

FIG. 1 shows a diagram of an imaging system according to one embodiment. The imaging system (1) shown comprises a light source (2) arranged so as to emit an optical signal (3). The light source (2) is coupled to an optical support (4) arranged so as to project an optical excitation signal with a substantially constant light intensity (5) originating from the signal (3) emitted by the source towards the body (6) to be analysed when using the system (1).

The optical support (4) is also arranged so as to receive the light (7) backscattered by the body (6) to be analysed. In one embodiment, the backscattered light can undergo different processing operations depending on the type of processing operations performed after image capture (OPF processing operations, SDF processing operations, etc.). The optical support (4) is also optically coupled to an asynchronous vision sensor (8), such that the asynchronous vision sensor (8) can react to events carried by the backscattered light signal (7). The asynchronous vision sensor (8) is equipped with an interface (9) for the output of an asynchronous signal, on which the different processing operations can be performed for the application being considered.

The light source (2) can, for example, be a light-emitting diode light source continuously supplied by an electric power source, or it can be a laser source or an incoherent light source.

In one embodiment, a focusing system (not shown in the figure) is positioned in the optical support (4) between the light source (2) and the body (6) to be analysed in order to focus the optical excitation signal (5) projected on said body. The focal distance of the focusing system, which can, for example, include a lens, will in practice be chosen depending on the desired analysis resolution and the light source used.

The optical excitation signal (5) is partially absorbed by the body (6) to be analysed, which backscatters the light in the form of a backscattered light signal (7). The optical support (4) is arranged so as to receive said backscattered light signal (7), and transport it after any optical processing operations, to the asynchronous vision sensor (8).

Figure 2:
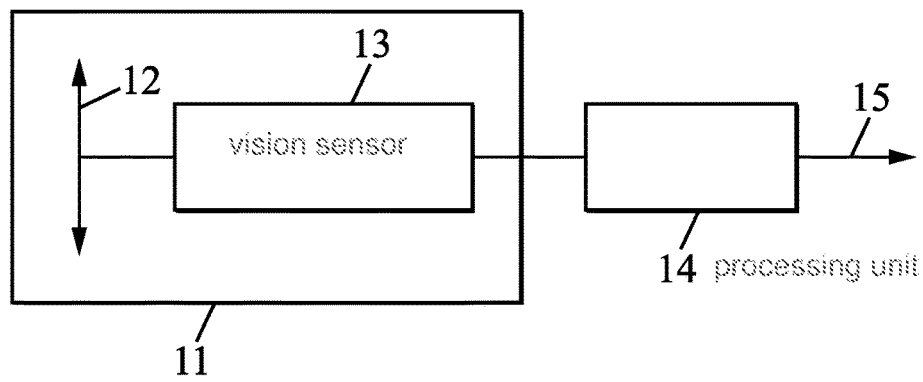
FIG. 2 is a block diagram of an asynchronous camera of an imaging device according to one embodiment of the device proposed.

FIG. 2 diagrammatically shows an asynchronous camera according to one embodiment of the imaging system.

The asynchronous camera (10) is capable of generating a signal carrying the asynchronous information representing, for each pixel of a pixel array, events respectively corresponding to variations in light captured by the camera. Depending on the application considered, the asynchronous camera (10) can be coupled in an operational manner to a viewing subsystem and/or to a processing and analysis subsystem, each subsystem comprising an input interface, configured to receive a signal carrying the asynchronous information.

The signal carrying the asynchronous information transiting over the coupling interface between the subsystems can have different forms, or formats, corresponding to different embodiments of the system. The output interface of the asynchronous camera (10) can also be provided such that it conforms to the different standard formats, such as the USB format. The system proposed is not limited to a specific asynchronous information format, a vector format for said information (for example an asynchronous signal carrying information representative of an events flow), or a specific output interface format of the asynchronous camera (10).

In one embodiment, the asynchronous signal generated at the output of the asynchronous camera (10) carries information representative of time events corresponding to variations in light captured by the camera (10).

With reference to FIG. 2, the asynchronous camera (10) including a light acquisition device (11) comprising an event-based asynchronous vision sensor (13) placed opposite a scene to be observed and receiving the light flow from the scene through an optical acquisition system (12). The optical acquisition system (12) can comprise a lens, the characteristics of which (in particular the focal length and diameter of which) are chosen to suit the characteristics of the sensor (13). The sensor (13) can comprise a group of photosensitive elements organised into a pixel array, such that each pixel of the array corresponds to a photosensitive element of the sensor. For each pixel of the array, the device (11) produces an event-based asynchronous signal sequence from the variations in light perceived by the pixel in the scene appearing in the field of vision of the device (11). Each pixel corresponding to a photosensitive element, therefore produces time events respectively corresponding to variations in light.

The sensor (13) therefore does not produce video frames constituted by the pixel array corresponding to the photosensitive elements of the sensor at a predetermined sampling frequency. It reacts for each pixel of the array to events corresponding to variations in light for the pixel. Conversely, it does not produce information for a pixel if no event takes place for said pixel. In particular, it does not systematically capture the light intensity of the pixels of the array. Therefore, the events to which it reacts are asynchronous, and do not depend on a video frame acquisition frequency. The camera (10) is therefore asynchronous, in particular in that it does not need any time reference defining a rhythm for the acquisition of information on the level of the light received by the pixels of the array. Each pixel sends its information in an asynchronous manner with regard to the other pixels of the array. This results in a significant reduction, or even elimination, of the redundancies created by the acquisition of video frames at a determined rhythm, not taking into account the absence of changes to the information carried by a pixel from one frame to another.

Conversely, a conventional camera will be controlled by a set of control and time synchronisation signals independent from the source of the visual information, for example a pixel acquisition clock signal (typically operating at a rhythm of several MHz), the rhythm of which will define a frequency at which a set of pixels of the array will be acquired. The temporal resolution, corresponding to the minimum time interval during which the camera can detect a change, will therefore be much lower for a conventional camera (for example a CCD or CMOS camera) (equal to about one ms) than that of an asynchronous camera (equal to about one µs).

A processing unit (14) processes the information originating from the sensor (13) and representative of the events taking place, in an asynchronous manner by the different pixels, in order to generate an asynchronous signal (15) carrying said information.

In one embodiment, the sensor (13) independently detects for each pixel the relative changes, and triggers, in an asynchronous and individual manner for the pixel, a measurement of the exposure value or grey level when—and immediately after—a change in luminosity of a predetermined amplitude occurs in the field of vision of the pixel.

In a general manner, the sensor (13) generates respective asynchronous signal sequences that represent events regarding the pixels of the array. In one specific embodiment, each asynchronous signal sequence indicates, or signals, events regarding a pixel, independently from the other signal sequences. It can, for example, include data that identifies events with their respective characteristics.

In one embodiment, the processing unit (14) comprises a processor operationally coupled to a memory. The memory can contain software instructions which, when run by the processor of the data processing unit cause said unit to process the signals received from the sensor and generate the asynchronous information representing, for each pixel, events corresponding to variations in light concerning the pixel, and transmit the asynchronous information over an output interface. The processing unit can be a component implementing a processor or a computing unit for generating the asynchronous information according to the different methods described and for controlling the asynchronous vision sensor of the device (11) within the asynchronous camera (10).

Furthermore, the processing unit, and in particular its processor and/or its memory means can be, separately or jointly, implemented in software form, as described hereinabove, in hardware form, such as an application-specific integrated circuit (ASIC), or in the form of a combination of hardware and software elements, for example one or more software programs intended to be loaded and run respectively on one or more FPGA-type (Field Programmable Gate Array) components. They can be implemented, separately or jointly, in the form of an electronic circuit, or within one or more electronic components (chip or chipset).

Figure 3A:
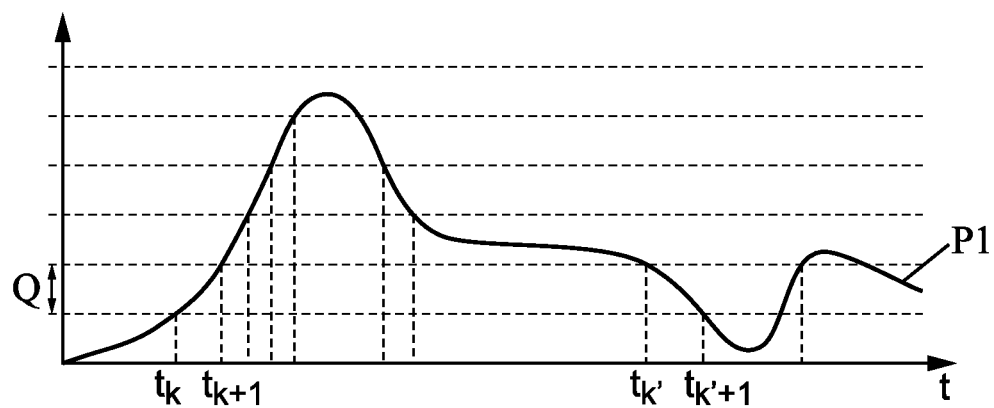
FIG. 3a is a diagram showing an example of a light intensity profile at the level of a pixel of an asynchronous camera.
Figure 3B:
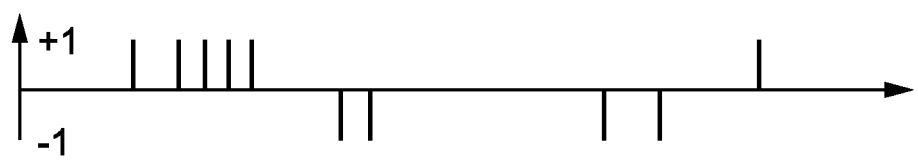
Figure 3C:
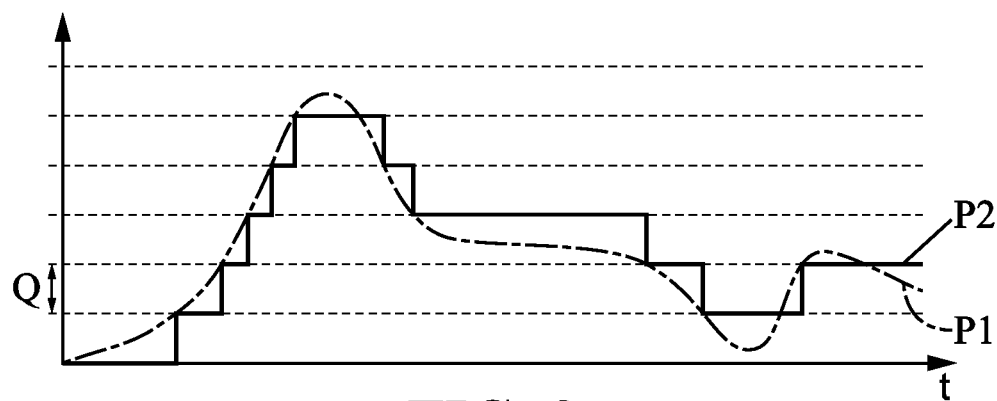
FIG. 3c shows the reconstruction of the intensity profile from the signal in FIG. 3b.

One example of an acquisition principle using an asynchronous sensor is shown in FIG. 3a-3c. According to this example, the information consists of a succession of moments in time, referenced $t_k$ (k=0, 1, 2, etc.) to which an activation threshold Q is reached. The sensor (13) is therefore provided with a variation detector which, for each pixel, measures and records the light intensity of the pixel when said intensity has varied beyond a threshold Q.

FIG. 3a shows an example of a light intensity profile P1 viewed by a pixel of the array of the asynchronous vision sensor. Each time that said intensity increases by a quantity equal to the activation threshold Q with respect to what it was at the moment in time $t_k$, a new event is identified and a positive line (level +1 in FIG. 3b) is emitted, corresponding to the moment in time at which the differential threshold Q is exceeded, referenced $t_{k+1}$. Symmetrically, each time that the intensity of the pixel reduces by the quantity Q with respect to what it was at the moment in time $t_k$, a new event is identified and a negative line (level −1 in FIG. 3b) is emitted, corresponding to the moment in time at which the differential threshold Q is exceeded, referenced $t_{k'+1}$. The asynchronous signal sequence for the pixel therefore consists of a succession of positive or negative pulses or lines, positioned in time at moments $t_k$ dependent on the light profile for the pixel. These lines can be mathematically represented by positive or negative delta functions and each characterised by an emission moment $t_k$ and a sign bit. The information corresponding to an event for a pixel, can include a first information item regarding a moment of occurrence of the event, and a second information item regarding a light characteristic for the pixel at this moment in time.

The form of the asynchronous information item for a pixel can be different from a succession of delta functions, whereby the events represented can have any time width or amplitude or waveform.

The output signal of the asynchronous camera (10) corresponds to what is known as an address-event representation (AER): an event-based signal sequence corresponds to each pixel.

FIG. 3c shows the intensity profile P2 that can be reconstructed as an approximation of the profile P1 by integration in time of the asynchronous signal in FIG. 3b.

Figure 4A:
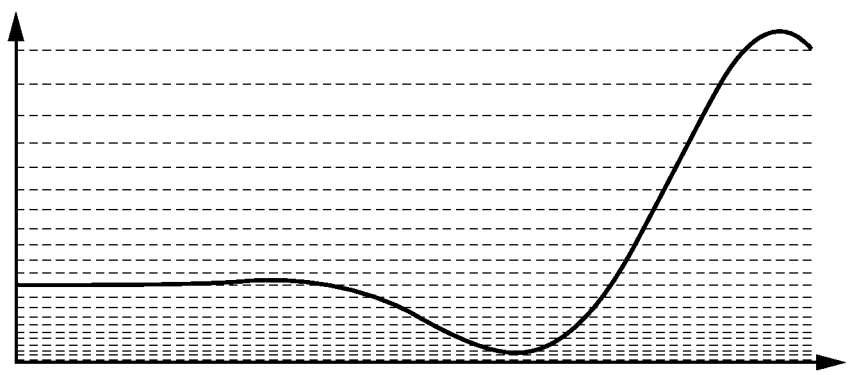
FIG. 4a-4b are diagrams similar to those in FIGS. 3a and 3b showing a light acquisition mode that can be used in another embodiment of the method.
Figure 4B:
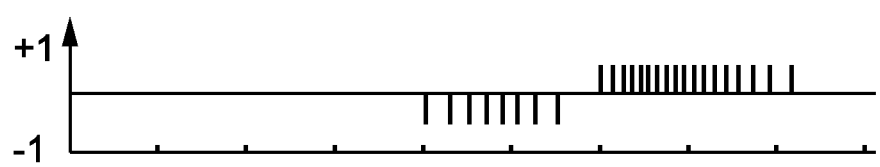

The activation threshold Q can be fixed, as is the case in FIG. 3a-3c, or capable of adapting to the light intensity, as is the case in FIGS. 4a and 4b. For example, the threshold ±Q can be compared to the variations in the logarithm of the light intensity for the generation of an event ±1.

The class of asynchronous photosensitive sensors generating events from variations in light intensity is referred to by the acronym DVS for Dynamic Vision Sensor.

For the purpose of illustration, the asynchronous vision sensor (13) can be a DVS sensor of the type described in "A 128×128 120 dB 15 µs Latency Asynchronous Temporal Contrast Vision Sensor", P. Lichtsteiner, et al., IEEE Journal of Solid-State Circuits, Vol. 43, No. 2, February 2008, pp. 566-576, or in the patent application US 2008/0135731 A1.

Another generation of asynchronous photosensitive sensors can be used to generate the asynchronous information item indicating events in addition to an associated characteristic, for example a grey level.

The article by Posch, C., Matolin, D., and Wohlgenannt, R. (2011) entitled "A qvga 143 db dynamic range frame-free pwm image sensor with lossless pixel-level video compression and time-domain cds", and published in the IEEE Journal of Solid-State Circuits, 46, pages 259-275. doi: 10.1109/JSSC.2010.2085952, provides a description of example events encoded by grey levels.

The asynchronous information for each pixel again consists of a succession of pulses or lines, positioned in time at moments in time $t_k$ dependent on the light profile for the pixel. Each event can, for example, correspond to two successive pulses, the first indicating the moment in time of the event and the second being used to determine a grey level for the pixel depending on the time difference between the two pulses. The information corresponding to an event for a pixel thus includes a first information item regarding a moment of occurrence of the event, and a second information item regarding a light characteristic (grey level) for the pixel at this moment in time.

For example, the detection of an event for a given pixel can be materialised by the generation by the sensor (13) of a first signed pulse identifying the event (for example a positive event for increasing illumination of the pixel, and a negative event for decreasing illumination of the pixel), and a second pulse to characterise the quantity of light detected: if the variation in light is slow, the difference between the two pulses will be long, which will show a low quantity of light, and therefore a dark grey level. There will be enough variation in light to trigger the detection of an event, however there will be little light during this variation. Conversely, if the variation in light is fast, the difference between the two pulses will be low, which will show a high quantity of light, and therefore a low grey level.

The pulse train generated by the sensor (13) can be transmitted to the processing unit (14), which will generate, on this basis, event information for the pixel, such as time difference information with regard to the previous event for the pixel, information on the grey level associated with the event for the pixel, positional information (for example in the form of coordinates (x, y) in the pixel array) of the pixel for which the event has been detected, and directional information regarding the variation in light detected for the pixel (increasing or decreasing).

This event information for each pixel will be multiplexed in order to generate an output signal (15) of the asynchronous camera (10).

By way of example, the asynchronous camera (10) can, in one embodiment, incorporate a new-generation event-based asynchronous vision sensor (13), sometimes referred to by the acronym ATIS, short for Asynchronous Time-Based Image Sensor". The asynchronous camera and the ATIS incorporated therein can, for example, be of the type described in the article by C. Posch et al., entitled "An Asynchronous Time-based Image Sensor" (IEEE International Symposium on Circuits and Systems, 2008, pages 2130-2133), or of the type described in the article by C. Posch et al., entitled "A QVGA 143 dB dynamic range frame-free PWM image sensor with lossless pixel-level video compression and time-domain CDS" (46(1):259275, 2011).

Another example of an ATIS vision sensor that can be used in the imaging system proposed is described in the article by T. Delbruck, P. Lichsteiner, and C. Posch, entitled "A 128×128 120 dB 15 µs latency asynchronous temporal contrast vision sensor" (IEEE Journal of Solid-State Circuits, Vol. 43, NO. 2, February 2008, p. 566-576). This CMOS, which has a 128×128 pixel array, is used to reach a dynamic range exceeding 120 dB for a temporal resolution of 15 µs.

For an asynchronous camera, the temporal resolution can therefore be defined by the minimum time difference between two pulses that can be generated by the camera depending on the variations in light intensity for a pixel. The examples mentioned hereinabove indicate that, for an ATIS camera, the temporal resolution achieved can equal about one µs, i.e. a significant gain when compared to conventional cameras (operating with a frame clock or a pixel clock).

This significant gain in temporal resolution is advantageous for the implementation of the imaging systems proposed, which can offer unequalled performance levels for observing and analysing dynamic phenomena. This is the case, for example, in the field of the observation and analysis of microcirculation of the blood, where asynchronous cameras can be used in an imaging system to measure the physiological parameters of blood cells (and in particular of red blood cells or RBC) such as the speed, trajectory and quantity of light sent at different wavelengths.

Similarly, the dynamic performance that can be obtained using a DVS or ATIS-type sensor is significantly greater than that which can be achieved with a conventional video camera having a realistic sampling frequency. For example, a sensor of this type can reach temporal resolutions of about one microsecond with a brightness range of greater than 120 dB, which is significantly greater than a standard CMOS/CCD camera that typically has a brightness range of 60-70 dB.

Figure 5:
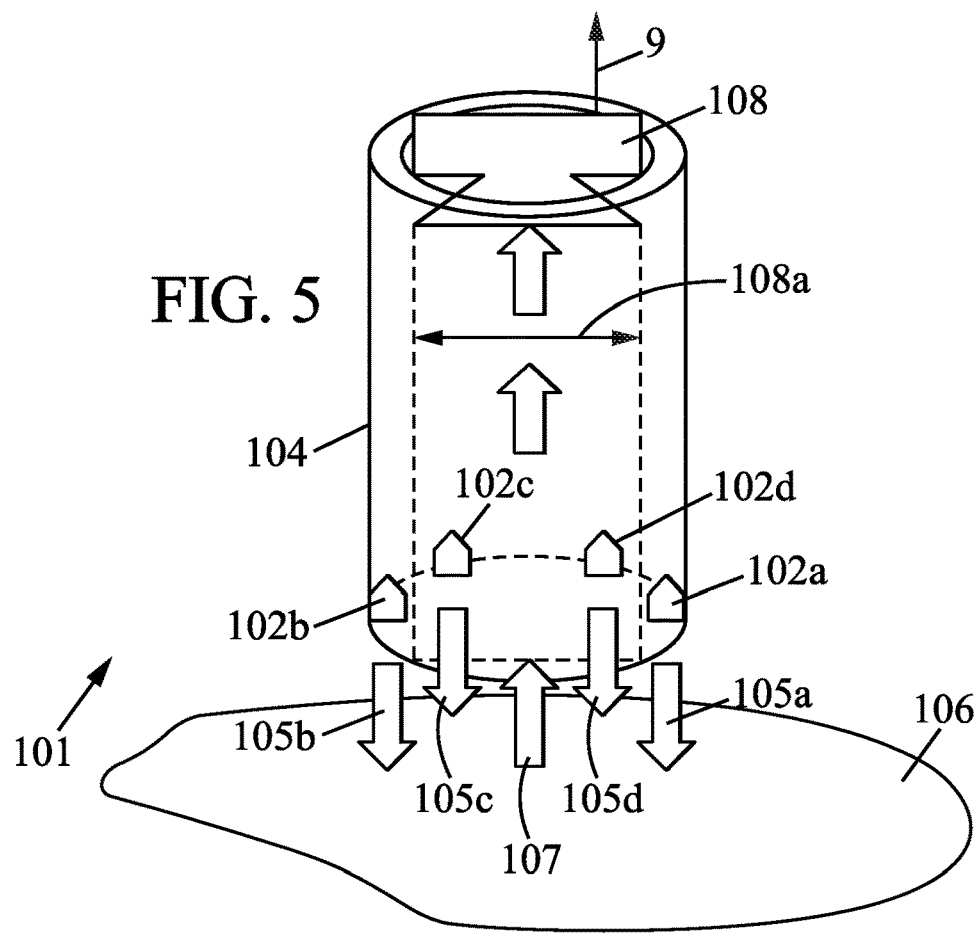
FIG. 5 is a block diagram of an imaging device according to one embodiment of the device proposed.

FIG. 5 shows a block diagram of an imaging system using the principle of dark-field microscopy according to one embodiment. The imaging system (100) shown includes an optical support (104) capable of being arranged in a hollow cylinder. One or more electroluminescent diodes (102a-102d) are mounted on one of the ends of the cylinder of the optical support (104) and arranged on the section of the cylinder so as to form an illuminating ring illuminating the body (106) to be analysed by projecting a plurality of optical signals with substantially constant respective light intensities.

These LEDs (102a-102d) forming a set of light sources could be replaced or complemented by laser diodes in another embodiment. The LED sources have the advantage of allowing for the generation of a spread-spectrum optical signal, which is a useful property, for example for analysing the speed of blood cells in a microcirculatory analysis application. The signal emitted by a laser source will be spectrally narrower.

These light sources are therefore arranged on the optical support (104) so as to each project an optical excitation signal (105a-105d) towards the body (106) to be analysed when using the system (101).

In one embodiment, optical processing operations can be performed on the signals emitted by the light sources (for example focusing, amplification, etc.) so that the excitation signal projected on the body to be observed is indirectly originating from the light sources.

The optical support (104) is also arranged so as to receive the light (107) backscattered by the body (106) to be analysed inside the hollow cylinder, said inner tube forming a dark area in which the backscattered light (107) is carried towards the asynchronous camera (108). The asynchronous camera (108) is positioned at the end of the hollow cylinder forming the optical support (104) that is opposite that at which the light sources (102a-102d) are arranged, such that the backscattered light crosses its optical acquisition system (108a) and illuminates its vision sensor when the system (101) is in use. The camera (108) is also equipped with an output interface (109) of an imaging signal, on which the different processing operations can be performed for the application being considered.

This configuration of the optical support (104) allows for the creation of a luminous ring that lights up the tissues to be analysed in the case of a dark-field microcirculatory analysis application, in addition to a dark area in which the backscattered light is carried, thus allowing for better contrast when the system is positioned near the body to be analysed, minimising the glare linked to the backscattering of the upper layers of the body studied.

Indeed, the device is used to project a large quantity of light via the luminous ring while only analysing the parts of the body studied that are not directly illuminated, through the analysis of the backscattered light originating from the central area of the illuminating ring.

In one embodiment, the light sources (102a-102d) are arranged so as to respectively emit the red, green, and/or infrared light, depending on the post-processing operations performed. The light sources can, for example, be configured such that a first source emits red light, a second source emits green light, and a third source emits infrared light. The light sources can therefore be configured to emit, together when using the device, light signals at different respective wavelengths. Indeed, the quantity of light absorbed by the tissues in the case of microcirculatory analysis, is seen to depend on the wavelength emitted. For example, red and infrared lighting can be used to analyse oxygenation of the blood.

Although FIG. 5 shows a block diagram of an imaging device operating according to the principle of dark-field microscopy, the device proposed is not limited to any specific imaging technology, and could implement, in other embodiments, any type of imaging technology, for example polarisation analysis imaging technology (OPS).

Figure 6:
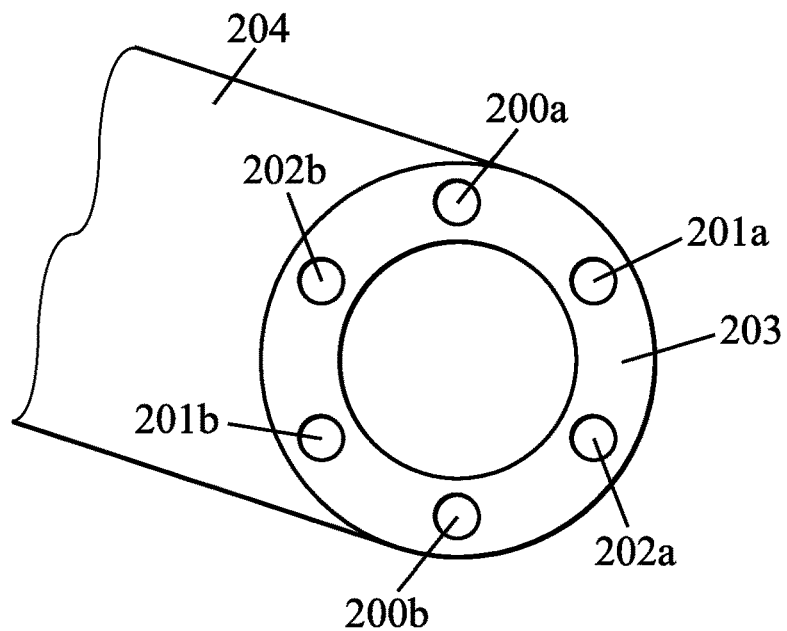
FIG. 6 is a block diagram of a portion of an imaging device according to one embodiment of the device proposed.

In one embodiment shown in FIG. 6, the imaging device proposed will include at least 6 light sources, including 2 red light sources (200a, 200b), 2 green light sources (201a, 201b), and 2 infrared light sources (202a, 202b), for example mounted on the end (203) of a hollow cylinder of an optical support (204) of the device.

Figures 7A, 7B:
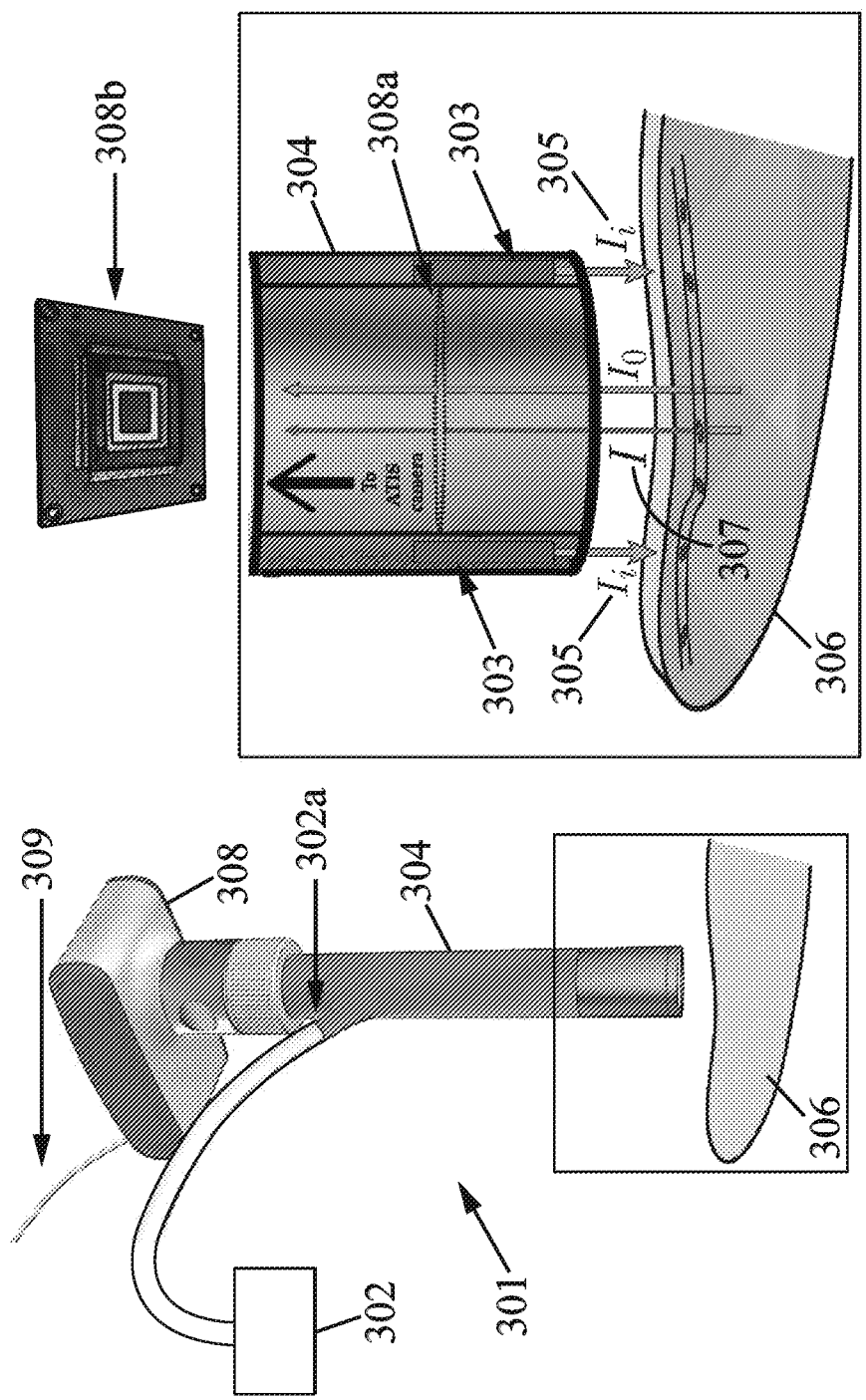

FIG. 7a shows an alternative embodiment of the device in FIG. 5, in which one or more light sources (302) are optically coupled to the optical support (304) of the device by optical fibres (302a). The optical support is shaped into a hollow cylinder, on one of whose ends an asynchronous camera (308) is mounted by mechanical coupling. The signal generated by the asynchronous camera (308) is produced on an output interface (309) of the camera (308), for example a USB-type connection.

FIG. 7b is a partial diagrammatic view of the device (301) in FIG. 7a, and shows an ATIS vision sensor (308b) and the optical acquisition system (308a) of the ATIS camera (308) placed at the main focal point of this optical acquisition system (308a), for example in order to capture images of a blood cell of a body observed (306) in a block of 3×3 pixels.

FIG. 7b also shows the internal structure of the optical support (304) in which one or more light guides are arranged, said light guides being coupled to optical fibre input connections or, depending on the embodiment, one or more ducts shaped for the insertion therein of one optical fibre end (303), in order to carry the incident light originating from the one or more light sources (302). The optical support (304) is therefore optically coupled to the light source (302) and arranged so as to project a luminous excitation signal with a substantially constant light intensity (305) (incident light 1) from the light source (302) towards a body (306) to be observed when using the device (300). The backscattered light l and $l_0$ (307) is carried by the inner part of the cylinder of the optical support (304) towards the ATIS (308b).

Although FIGS. 7a and 7b show an imaging device operating according to the principle of dark-field microscopy, the device proposed is not limited to any specific imaging technology, and could implement, in other embodiments, any type of imaging technology, for example polarisation analysis imaging technology (OPS).

Figure 8:
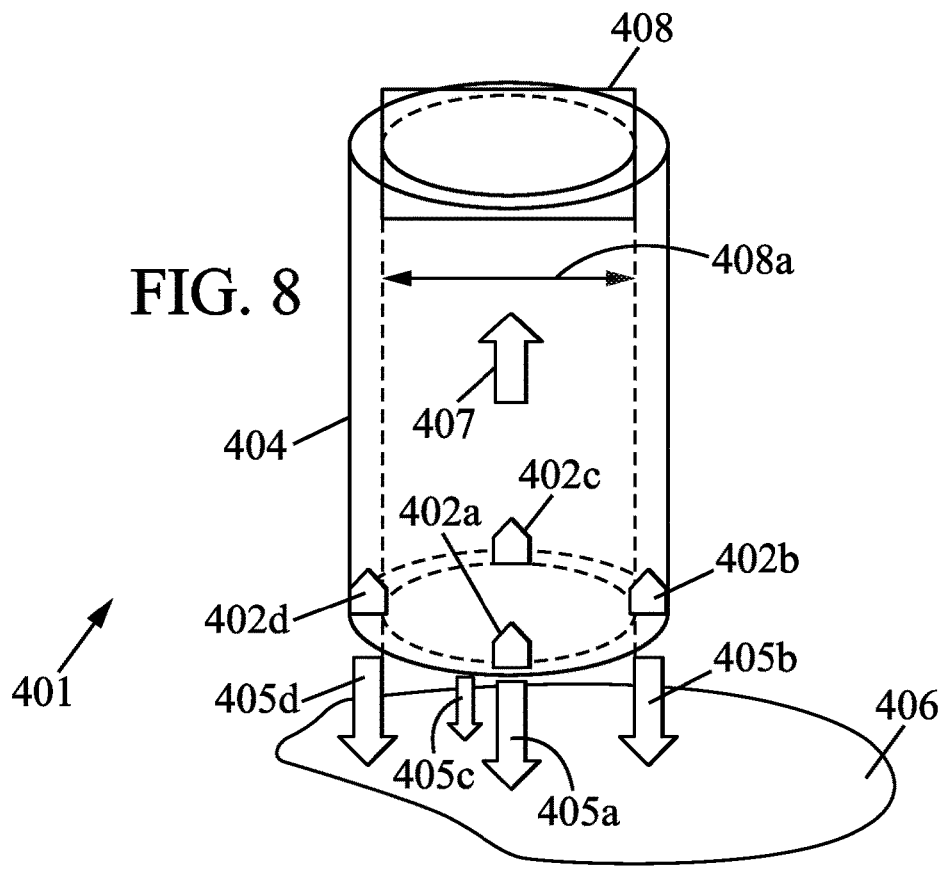
FIG. 8 is a block diagram of a multi-camera imaging device according to one embodiment of the device proposed.

FIG. 8 shows one embodiment in which the imaging device comprises a plurality of ATIS cameras. The ATIS cameras of the device are spatially arranged so as to substantially capture the same light signal backscattered by the body to be observed for the pixel.

FIG. 8 is a block diagram showing the imaging device (401) operating according to the principle of dark-field microscopy. The imaging system (401) shown includes an optical support (404) arranged in a hollow cylinder. One or more light sources (402a-402d), for example electroluminescent diodes and/or laser diodes, are mounted on one of the ends of the cylinder of the optical support (404) and arranged on the section of the cylinder so as to form an illuminating ring illuminating the body (406) to be analysed, by projecting a plurality of luminous excitation signals with a substantially constant intensity. These light sources (402a-402d) are therefore arranged on the optical support (404) so as to each project an optical excitation signal (405a-405d) towards the body (406) to be analysed when using the system (401). In one embodiment, optical processing operations can be performed on the signals emitted by the light sources (for example focusing, amplification, etc.) so that the excitation signals projected on the body to be observed are respectively indirectly originating from the light sources (402a-402d).

The optical support (404) is also arranged so as to receive the light (407) backscattered by the body (406) to be analysed inside the hollow cylinder, said inner tube forming a dark area in which the backscattered light (407) is carried towards the block of asynchronous sensors (408) when using the device. In the embodiment shown, the block of asynchronous sensors (408) is positioned at the end of the hollow cylinder forming the optical support (404) that is opposite that at which the light sources (402a-402d) are arranged, such that the backscattered light (407) crosses an optical acquisition system (408a) and illuminates the vision sensors of the block of asynchronous sensors (408) when the system (401) is in use. The asynchronous sensors of the block (408) can therefore use the same optical acquisition system (408a) in one embodiment. This embodiment is not however limiting, and each asynchronous camera of the device can have its own optical acquisition system, while being arranged so as to capture asynchronous events corresponding to variations in the light (407) backscattered by the body to be observed (406) for each pixel of its vision sensor.

The asynchronous cameras are also each equipped with an output interface (not shown in the figure) of an imaging signal, on which the different processing operations can be performed for the application being considered.

Although FIG. 8 shows a block diagram of a multi-camera imaging device operating according to the principle of dark-field microscopy, the device proposed is not limited to any specific imaging technology, and could implement, in other embodiments, any type of imaging technology, for example OPS technology.

Figure 9A:
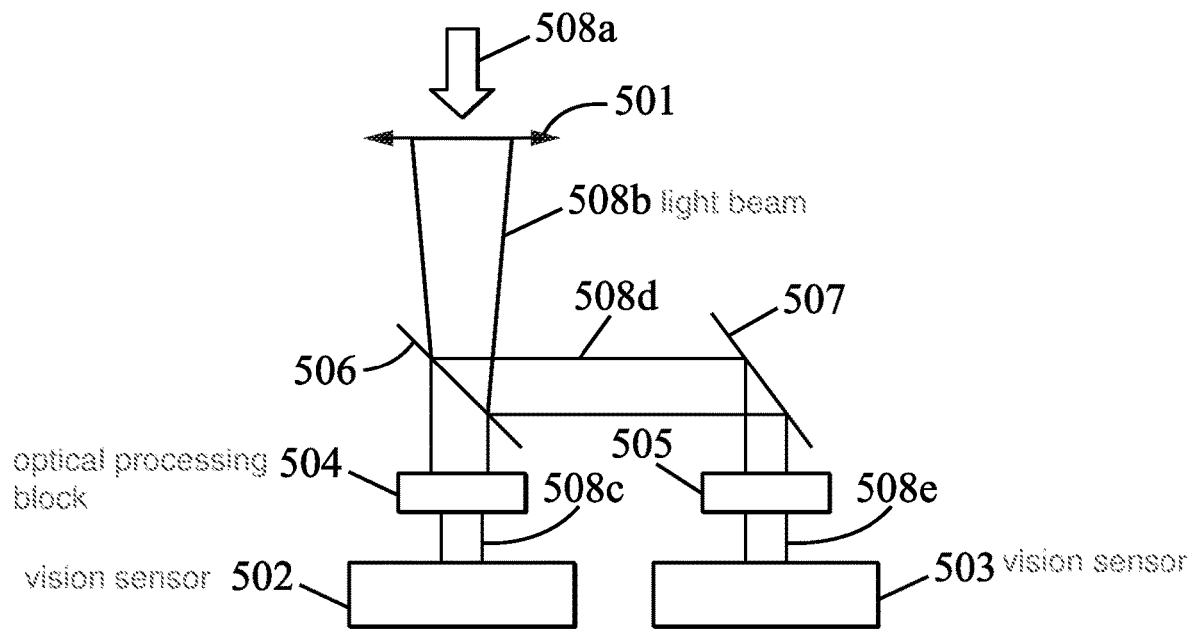
FIGS. 9a and 9b are block diagrams of portions of multi-camera imaging devices according to different embodiments of the device proposed.
Figure 9B:
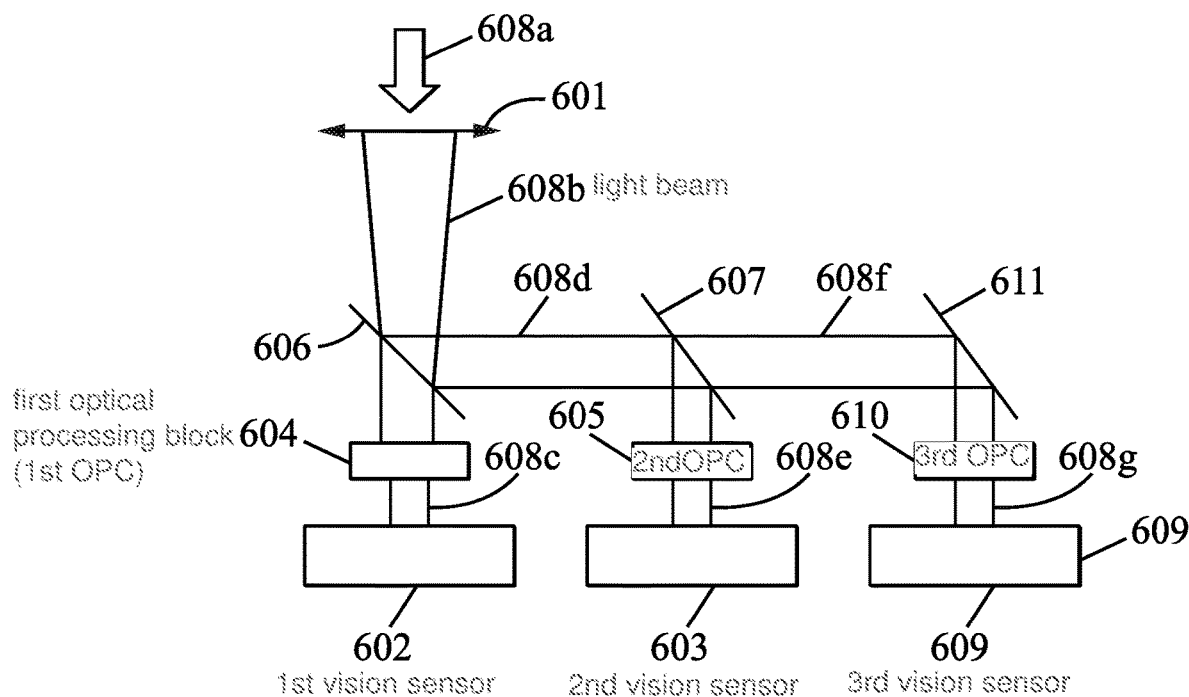

FIGS. 9a and 9b show one embodiment of blocks of two and three asynchronous sensors respectively.

With reference to FIG. 9a, the light (508a) backscattered by the body to be observed crosses an optical acquisition system (501) of an asynchronous camera of the imaging device proposed, and produces a light beam (508b), that partially crosses and is partially reflected on a dichroic mirror (506) arranged so as to split the light beam (508b) originating from the optical acquisition system (501) into two beams. The part of the light beam (508b) that is not reflected by the dichroic mirror (506) is processed by an optical processing block (504), for example in order to optically filter the light beam (508b), which generates at the output a light beam (508c) that illuminates a first asynchronous vision sensor (502). The part (508d) of the light beam (508b) that is reflected by the dichroic mirror (506) is reflected on a mirror (507) arranged so as to redirect the light beam (508d) originating from the optical acquisition system (501) and from the dichroic mirror (506) towards a second optical processing block (505) and asynchronous vision sensor (503) assembly. The reflected beam (508d) is thus processed by an optical processing block (505), for example in order to optically filter the light beam (508d), which generates at the output a light beam (508e) that illuminates a second asynchronous vision sensor (503).

These optical processing block and asynchronous vision sensor assemblies allow for the selection of certain characteristics of the signal that illuminates each asynchronous vision sensor, while ensuring that each signal originates from the light backscattered by the body to be observed, so that each sensor substantially observes the same scene. Therefore, each event detected by the asynchronous cameras corresponds to the same body. For example, within the scope of an application for observing and analysing microcirculation, each event detected with regard to the same blood cell at a given moment in time will be detected by each of the asynchronous sensors of the imaging device. The imaging device proposed in the asynchronous multi-camera embodiment is thus arranged so as to capture information on the same pixel (by assuming that a correspondence exists between the pixels of the arrays of the different asynchronous vision sensors) and at the same given moment in time, which prevents the spatial resolution of the observation from being reduced (as with a Bayer filter for example), while preserving the high temporal resolution obtained with asynchronous cameras.

For example, the optical processing blocks in FIG. 9a can include an optical filter so as not to allow red light to pass for one, and infrared light to pass for the other, in order to acquire imaging data used to determine an oxygenation rate of blood cells in an application for analysing microcirculation.

In more general terms, the multi-camera embodiment of the imaging device proposed can be used for spectral analyses of the light backscattered by the body to be analysed, using optical filters for each camera, said filters operating in a frequency band to be analysed.

With reference to FIG. 9b, the block of asynchronous vision sensors can include three optical processing and asynchronous sensor assemblies. The backscattered light (608a) crosses an optical acquisition system (601) which generates a beam (608b) that is partially reflected by a first dichroic mirror (606). The part of the beam (608b) that is not reflected by the first dichroic mirror (606) crosses a first optical processing block (604), which generates at the output a beam (608c) that illuminates a first asynchronous vision sensor (602).

The part (608d) of the beam (608b) that is reflected by the first dichroic mirror (606) is itself partially reflected on a second dichroic mirror (607) so that it is redirected towards a second optical processing block (605), which generates at the output a beam (608e) that illuminates a second asynchronous vision sensor (603).

The part (608f) of the beam (608d) that is not reflected by the second dichroic mirror (607) is reflected on a third mirror (611) so that it is redirected towards a third optical processing block (610), which generates at the output a beam (608g) that illuminates a third asynchronous vision sensor (609).

This embodiment of the imaging device using three asynchronous cameras allows for post-processing operations requiring the parallel capture of images of the body to be analysed.

With reference to FIGS. 9a and 9b, the dichroic mirrors shown are provided as an example of an optical component that can be used to split an incident beam into two beams. However, the arrangement of such optical components can vary according to the spatial configuration of the asynchronous vision sensors or asynchronous cameras.

In another embodiment, the imaging device proposed can have four embedded cameras. Three light sources (red, green and infrared) illuminate the sample in an indirect manner with, for example, a ring-shaped structure. The light backscattered by the sample to be analysed is therefore captured by an optical system located above a dark area for a device operating according to the principle of dark-field microscopy. The light is then distributed depending on its wavelength over the 4 cameras, for example by means of filters arranged along the path of the light before reaching the sensor of each camera: one asynchronous camera for red light, one asynchronous camera for infrared light, one asynchronous camera for green light and one conventional camera with high spatial resolution (for example 4 M pixels for a temporal resolution of 300 frames per second), also for green light.

Figure 10:
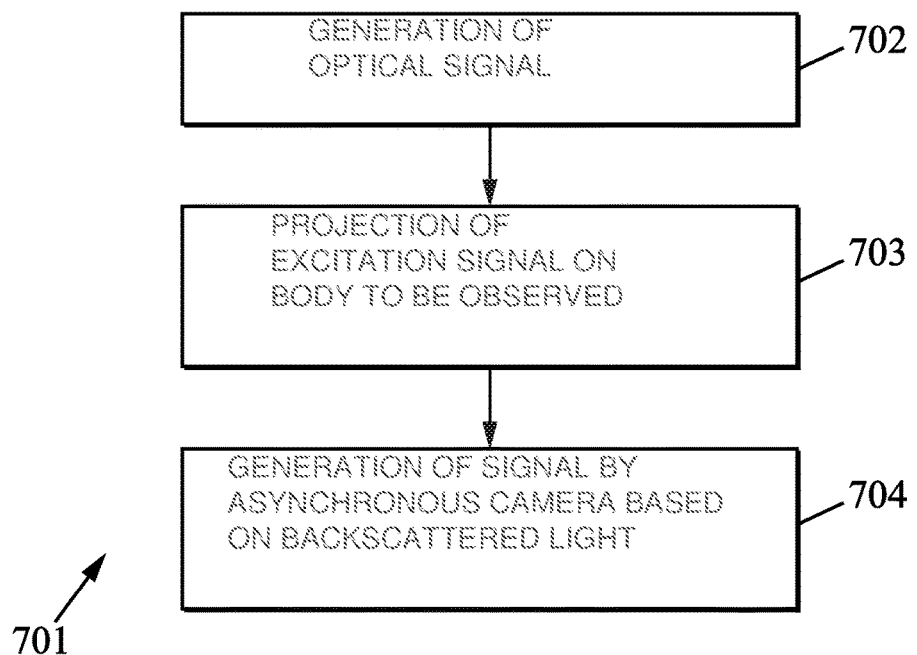
FIG. 10 is a diagram showing the imaging method proposed according to one embodiment.

FIG. 10 shows the imaging method (701) proposed according to one embodiment. In this embodiment, an optical signal is generated (702), from which is extracted a luminous excitation signal with a substantially constant light intensity. The luminous excitation signal can directly originate from the optical signal, or indirectly originate therefrom, after certain processing operations (focusing, frequency processing, polarisation processing, etc.). The luminous excitation signal is projected (703) onto the body to be observed, in order to capture the light backscattered by said body. At least one asynchronous sensor is used to generate (704) a signal comprising, for each pixel of the pixel array of the sensor, a signal sequence representing asynchronous events corresponding to variations in the light backscattered by the body to be observed for the pixel.

Although disclosed using a certain number of detailed embodiments, the method of controlling activation and the equipment for implementing the method include various alternatives, modifications and improvements that will be clearly apparent to one of ordinary skill in the art. It is understood that these different alternatives, modifications and improvements fall within the scope of the invention as defined by the claims hereinbelow.

Moreover, the different aspects and characteristics disclosed hereinabove can be implemented together or individually, or can substitute each other, and the collection of different combinations and sub-combinations of the aspects and characteristics fall within the scope of the invention. Furthermore, some of the systems and equipment disclosed hereinabove do not include all of the modules and functions disclosed for the preferred embodiments.

The information and signals disclosed herein can be represented according to a multitude of technologies and techniques. For example, the instructions, messages, data, commands, information, signals, bits and symbols can be represented by voltages, intensities, electromagnetic waves or a combination thereof.

Depending on the embodiment chosen, certain acts, actions, events or functions of each of the methods described herein can be performed or can take place in a different order to that disclosed, or can be added, merged or not be performed or not take place, depending on the case. Moreover, in certain embodiments, certain acts, actions or events are performed or take place simultaneously and not successively.

The invention claimed is:

1. An imaging device comprising:
   at least one light source arranged so as to generate an optical signal;
   an optical support coupled to the at least one light source, the optical support arranged so as to project a luminous excitation signal with a constant light intensity from the at least one light source to a body to be observed when using the device; and
   a first asynchronous camera coupled to the optical support and designed so as to generate a signal comprising, for each pixel of a first pixel array, a signal sequence representing asynchronous events corresponding to variations in the light backscattered by the body to be observed for the pixel.

2. The device according to claim 1, comprising a second asynchronous camera coupled to the optical support and designed so as to generate a signal comprising, for each pixel of a second pixel array, a signal sequence representing asynchronous events corresponding to variations in the light backscattered by the body to be observed for the pixel, and wherein a first optical filter is arranged so as to filter the backscattered light captured by the first asynchronous camera.

3. The device according to claim 2, wherein a second optical filter is arranged so as to filter the backscattered light captured by the second asynchronous camera.

4. The device according to claim 3, comprising a third asynchronous camera coupled to the optical support and designed so as to generate a signal comprising, for each pixel of a third pixel array, a signal sequence representing asynchronous events corresponding to variations in the light backscattered by the body to be observed for the pixel, and wherein a third optical filter is arranged so as to filter the backscattered light captured by the third asynchronous camera.

5. The device according to claim 1, wherein the at least one light source is a light-emitting diode or a laser source.

6. The device according to claim 1, wherein the at least one light source comprises a plurality of light sources arranged on the optical support so as to generate luminous excitation signals with constant respective light intensities.

7. Device according to claim 6, wherein the light sources are also arranged on the optical support such that they form a luminous ring.

8. The device according to claim 1, wherein the asynchronous camera is arranged on the support located above an area not illuminated by the at least one light source.

9. A microcirculation imaging system comprising an imaging device comprising:
   at least one light source arranged so as to generate an optical signal;
   an optical support coupled to the at least one light source, the optical support arranged so as to project a luminous excitation signal with a constant light intensity from the at least one light source to a body to be observed when using the device; and
   a first asynchronous camera coupled to the optical support and designed so as to generate a signal comprising, for each pixel of a first pixel array, a signal sequence representing asynchronous events corresponding to variations in the light backscattered by the body to be observed for the pixel.

10. An imaging method comprising:

generating an optical signal;

projecting a luminous excitation signal with a constant light intensity from the optical signal to a body to be observed; and generating a signal comprising, for each pixel of a first pixel array, a signal sequence representing asynchronous events corresponding to variations in the light backscattered by the body to be observed for the pixel.

\* \* \* \* \*